(12) United States Patent
Davis et al.

(10) Patent No.: US 11,896,825 B2
(45) Date of Patent: Feb. 13, 2024

(54) APPARATUS AND METHODS FOR OPPOSING TORQUE IMPARTED ONTO COCHLEAR IMPLANT MAGNETS BY MAGNETIC FIELDS

(71) Applicant: ADVANCED BIONICS AG, Staefa (CH)

(72) Inventors: Austin Charles Davis, North Hollywood, CA (US); James George Elcoate Smith, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 354 days.

(21) Appl. No.: 17/278,316

(22) PCT Filed: Oct. 4, 2018

(86) PCT No.: PCT/US2018/054275
§ 371 (c)(1),
(2) Date: Mar. 21, 2021

(87) PCT Pub. No.: WO2020/072055
PCT Pub. Date: Apr. 9, 2020

(65) Prior Publication Data
US 2021/0330975 A1    Oct. 28, 2021

(51) Int. Cl.
| | | |
|---|---|---|
| A61N 1/37 | (2006.01) | |
| A61N 1/36 | (2006.01) | |
| A61N 1/08 | (2006.01) | |
| A61F 5/058 | (2006.01) | |
| A61F 13/12 | (2006.01) | |
| A61N 1/05 | (2006.01) | |
| A61N 1/372 | (2006.01) | |

(52) U.S. Cl.
CPC ...... *A61N 1/36038* (2017.08); *A61F 5/05891* (2013.01); *A61F 13/12* (2013.01); *A61N 1/0541* (2013.01); *A61N 1/086* (2017.08); *A61N 1/372* (2013.01)

(58) Field of Classification Search
CPC .. A61N 1/36038; A61N 1/086; A61N 1/0541; A61N 1/372; A61F 5/05891
See application file for complete search history.

(56) References Cited

U.S. PATENT DOCUMENTS

| | | |
|---|---|---|
| 3,724,453 A | 4/1973 | Dixon et al. |
| 3,759,256 A | 9/1973 | O'Malley |
| 5,337,760 A | 8/1994 | Nichols |
| 6,488,617 B1 | 12/2002 | Katz |

(Continued)

FOREIGN PATENT DOCUMENTS

| | | |
|---|---|---|
| CN | 209915995 U | 1/2020 |
| WO | WO 2010/070340 A1 | 6/2010 |

OTHER PUBLICATIONS

PCT International Search and Written Opinion dated Jun. 7, 2019 for PCT App. Ser. No. PCT/US2018/054275.

(Continued)

*Primary Examiner* — Eric D. Bertram
(74) *Attorney, Agent, or Firm* — Henricks Slavin LLP

(57) ABSTRACT

An apparatus, for use with a cochlear implant having a magnet and implanted within a patient having first and second ears, includes a first splint and a strap system, including at least a forehead strap and a chin strap, configured to position the first splint behind the first ear.

11 Claims, 6 Drawing Sheets

(56) References Cited

U.S. PATENT DOCUMENTS

| | | | |
|---|---|---|---|
| 10,576,276 B2* | 3/2020 | Leigh | A61N 1/08 |
| 10,917,730 B2* | 2/2021 | Kennes | A61N 1/36038 |
| 2002/0123706 A1 | 9/2002 | Browd | |
| 2010/0286581 A1 | 11/2010 | Hipp et al. | |
| 2017/0312503 A1* | 11/2017 | Leigh | A61N 1/08 |
| 2022/0032048 A1* | 2/2022 | Von Huben | A61N 1/08 |

OTHER PUBLICATIONS

Med-El Mi1000 CONCERTO Surgical Guideline.
Cochlear™ Nucleus® Implant Bandage and Splint Kit for MRI (MRI Kit) Instructions.
Office Action dated Jun. 14, 2023 for EPO App. Ser. No. 18 795 864.0.

* cited by examiner

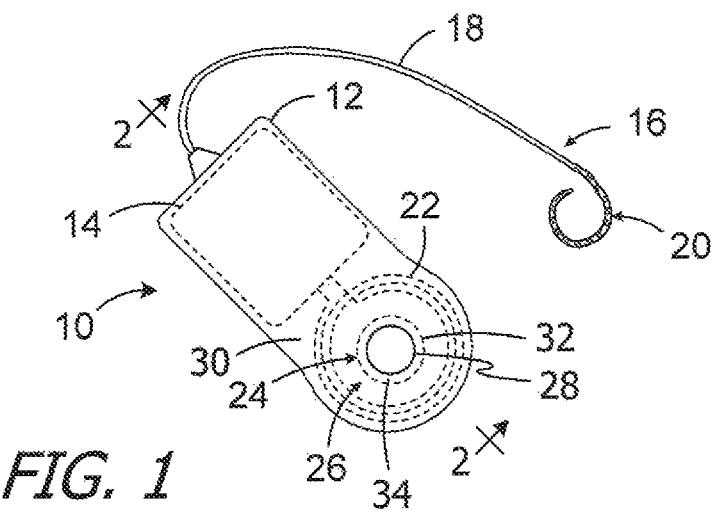
FIG. 1
Prior Art
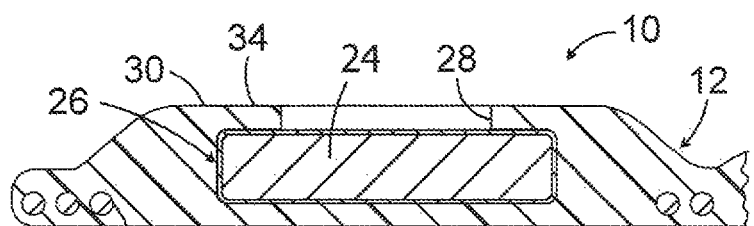
FIG. 2 - Prior Art
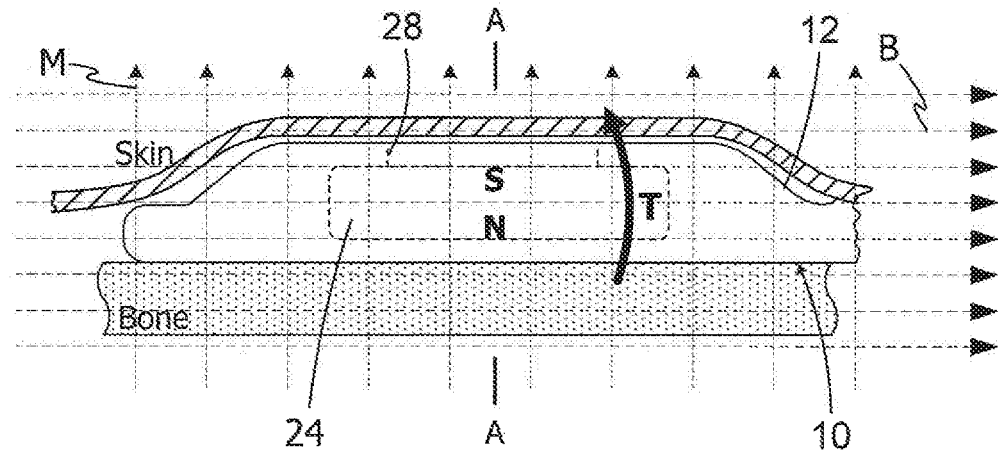
FIG. 3 - Prior Art

APPARATUS AND METHODS FOR OPPOSING TORQUE IMPARTED ONTO COCHLEAR IMPLANT MAGNETS BY MAGNETIC FIELDS

CROSS-REFERENCE TO RELATED APPLICATIONS

This application is the U.S. National Stage of PCT App. Ser. No. PCT/US2018/054275, filed Oct. 4, 2018.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

One example of a conventional cochlear implant (or "implantable cochlear stimulator") is the cochlear implant 10 illustrated in FIGS. 1 and 2. The cochlear implant 10 includes a flexible housing 12 formed from a silicone elastomer or other suitable material (e.g., with a hardness from 50 to 70 Shore A), a processor assembly 14, a cochlear lead 16 with a flexible body 18 and an electrode array 20, and an antenna 22 that may be used to receive data and power by way of an external antenna that is associated with, for example, a sound processor unit. The antenna 22 is located within an antenna portion 23 of the housing 12. A cylindrical positioning magnet 24, with north and south magnetic dipoles that are aligned in the axial direction of the disk, is located within the housing 12. The positioning magnet 24 is used to maintain the position of a headpiece transmitter over the antenna 22.

There are some instances where it is necessary to remove the magnet from a conventional cochlear implant, and then reinsert the magnet, in situ, i.e., with the cochlear implant accessed by way of an incision in the skin. To that end, the positioning magnet 24 is carried within an internal magnet pocket 26 and can be inserted into, and removed from, the housing pocket by way of a magnet aperture 28 that extends through the housing top wall 30. The magnet 22 is larger than the magnet aperture 28, i.e., the outer perimeter of the magnet is greater than the perimeter of the magnet aperture. The portion of the top wall 30 between the aperture 28 and the outer edge 32 of the magnet 24 forms a retainer 34 that, absent deformation of the aperture and retainer, prevents the magnet from coming out of the housing 12. During installation and removal, the aperture 28 and retainer 34 are stretched or otherwise deformed so that the magnet 24 can pass through the aperture 28.

Removal and reinsertion of the implant magnet by way of the aperture may be required because some conventional cochlear implants are not compatible with magnetic resonance imaging ("MRI") systems. As illustrated in FIG. 3, the implant positioning magnet 24 produces a magnetic field M in a direction that is perpendicular to the patient's skin and parallel to the axis A.

This magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may generate a significant amount of torque T on the implant magnet 24. The torque T may be sufficient to deform the retainer 34, dislodge the implant magnet 24 from the pocket 26, and cause reorientation of the implant magnet. Reorientation of the magnet 24 can place significant stress on the dermis (or "skin"), which cause significant pain. In some instances, the implant magnet 24 may rotate 180 degrees, thereby reversing the N-S orientation of the magnet.

As alluded to above, magnet rotation may be avoided by surgically removing the positioning magnet prior to the MRI procedure and then reinserting the magnet after the procedure. The present inventors have determined that removal and reinsertion can be problematic because some patients will have many MRI procedures during their lifetimes, and repeated surgeries can result in skin necrosis at the implant site. Another proposed solution to the problems associated with magnet rotation is disclosed in US Pat. Pub. No. 2017/0312503, involves the use of a resilient bandage (or "belt") and a splint. The splint is placed over the portion of the cochlear implant with the magnet, and the resilient bandage is tightly wrapped around the patient's head in a manner similar to a headband. The present inventors have determined that the bandage and splint methodology disclosed in US Pat. Pub. No. 2017/0312503 is susceptible to improvement. For example, tightening the bandage to an extent sufficient to hold the magnet in place can result in the bandage sliding upwardly toward the crown of the head, especially in those instances where the patient has long hair. It can also be difficult to maintain the desired position of the splint relative to the bandage and the cochlear implant during the wrapping process, especially in the case of patients with bilateral cochlear implants. In addition to inconvenience and possible magnet rotation during MRI procedures, the delays associated with sliding bandages and improperly positioned splints prevent efficient usage of the MRI systems.

SUMMARY

An apparatus, for use with a cochlear implant having a magnet and implanted within a patient having first and second ears, in accordance with at least one of the present inventions includes a first splint and a strap system, including at least a forehead strap and a chin strap, configured to position the first splint behind the first ear.

A method of preventing rotation of a first cochlear implant magnet implanted within the head of a patient having first and second ears, in accordance with at least one of the present inventions, includes the steps of positioning a first splint behind the first ear and over the first cochlear implant magnet, and pulling the first splint against the head with a forehead strap and a chin strap.

There are a number of advantages associated with such apparatus and methods. For example, the present straps can be tightened to an extent sufficient to hold the magnet in place without the forehead strap sliding upwardly toward the crown of the head. The present apparatus and methods also make it easier to position the splint(s) over the implant(s), as compared to the above-described wrapping process.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a conventional cochlear implant.

FIG. 2 is a section view taken along line 2-2 in FIG. 1.

FIG. 3 is a section view showing the conventional cochlear implant as an MRI magnetic field is being applied.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 4:
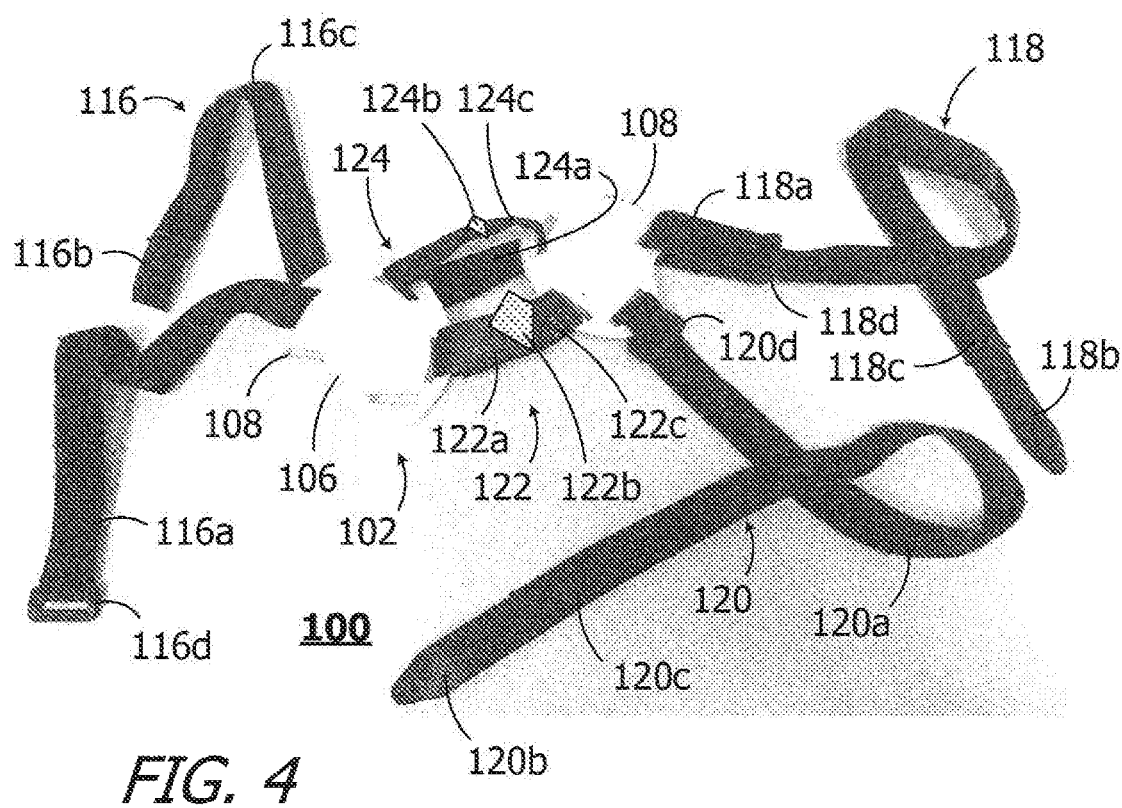
FIG. 4 is a plan view of an apparatus in accordance with one embodiment of a present invention.

One example of an apparatus for opposing torque imparted onto a cochlear implant magnet (or "apparatus") in accordance with the present inventions is generally represented by reference numeral 100 in FIG. 4. The exemplary apparatus 100 includes first and second splints 102 and a strap system 104 that maintains the splints in their intended locations. As discussed in greater detail below, the configuration of the strap system 104 allows the straps that pull the splints 102 against the head (i.e., against the hair, and against skull albeit with a thin layer of skin in between) to be tightened to an extent sufficient to hold the magnet in place without sliding upwardly toward the crown of the head, and maintains the splints in the desired position. Also, although some implementations may include a single splint, the use of first and second splints 102 in the illustrated implementation allows the same apparatus 100 to be used on patients with only a single cochlear implant, in either the right ear or the left ear, as well as on patients with bilateral cochlear implants (i.e., implants in both ears). The first and second splints 102 and strap system 104 may also be configured such that the splints do not overlap the ears when the straps are tightened.

Figure 5:
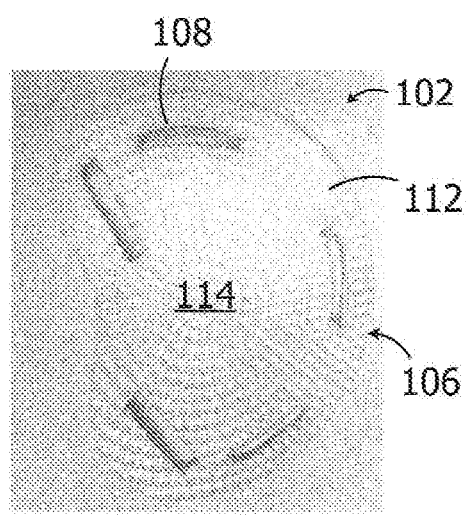
FIG. 5 is a plan view of a portion of the apparatus illustrated in FIG. 4.
Figure 6:
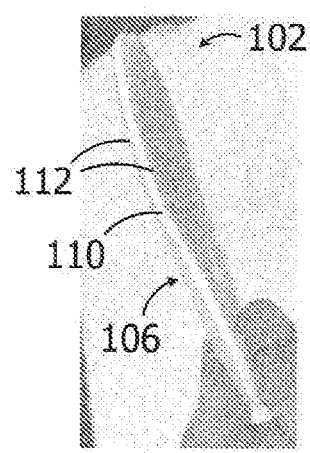
FIG. 6 is a side view of a portion of the apparatus illustrated in FIG. 4.

Referring to FIGS. 4-6, the exemplary splints 102 each include a relatively stiff splint body 106 that is sized and shaped for positioning behind ear. As used herein, a relatively stiff splint body is a splint body that is stiffer than the straps (described below) in the strap system and is sufficiently stiff to prevent rotation of an implanted cochlear implant magnet (e.g., implant magnet 24) when the associated cochlear implant is exposed to a MRI magnetic field. For example, the splints 102 may be rigid (i.e., will not flex during normal use), with a curvature that conforms to the user's head, or flexible enough to conform to the user's head yet stiff enough to prevent magnet rotation. In some instances, the material may have a Young's modulus of 0.5 GPa to 0.8 GPa. The splint body 106, which is kidney shaped in the illustrated implementation, includes strap apertures 108 and may be a multi-layer structure with an inner layer 110 and outer layers 112. For example, the outer layers 112 may be a relatively soft and flexible material (such as rubber) for patient comfort, while the inner layer may be relatively hard and stiff material (such as a flexible plastic, e.g., high-density polyethylene, or other polymer) to prevent magnet rotation. The outer layers 112 have roughened surfaces 114 that reduce the likelihood that the splints 102 will slide relative to the patient's head. Other exemplary splint configurations are described below with reference to FIGS. 12-18.

The exemplary strap system 104 illustrated in FIG. 4 includes a forehead strap 116 (or "frontal bone strap"), a pair of chin straps 118 and 120, and a pair of rear straps 122 and 124 (or "parietal bone straps"). Each strap 116-124 extends through a respective pair of strap apertures 108, with one strap aperture being on one splint 102 and the other aperture being on the other splint. The straps include respective strap bodies 116a, 118a, 120a, 122a, and 124a that are flexible (i.e., will readily bend to conform the patient's head) and may be either resilient, or inelastic, in the length dimension. In the illustrated implementation, the strap bodies 116a, 118a, 120a of the forehead and chin straps 116, 118 and 120 are resilient in the length dimension, and may be stretched around the head as discussed below, while the strap bodies 122a and 124a are inelastic in the length dimension and can be used to fix the distance between the splints 102. Suitable material for the resilient strap bodies 116a-120a includes but is not limited to nylon and woven elastics (e.g., formed from polyester and silicone rubber), while suitable material for the inelastic strap bodies 122a-124a includes but is not limited to high density polyethylene, polypropylene, leather, canvas fabric and vinyl.

The exemplary straps 116-124 may also be provided with fasters that secure portions of each strap to one another to fix the length of the straps. In the illustrated implementation, the exemplary straps 116-124 include respective hook material 116b-124b and respective loop material 116c-124c. The straps 116-120 also include buckles 116d-120d. In other instances, some or all of the straps may be provided with ratcheting systems, lock slider buckles or the like that allow the straps to be tightened to the desired extent and then released when appropriate.

The exemplary apparatus 100 may be worn on the head in the manner illustrated in FIGS. 7-10. Here, the forehead strap 116 passes over the forehead (or "frontal bone") F and through a strap aperture 108 in each splint 102. A portion of the forehead strap 116 passes through the buckle 116d and folds over itself so that hook and loop materials 116b and 116c (or other fasteners) can be secured to one another to fix the length/position of the forehead strap 116. The forehead strap 116 will typically be stretched, and in tension, to pull the splints 102 firmly against the patient's head H.

Figure 10:
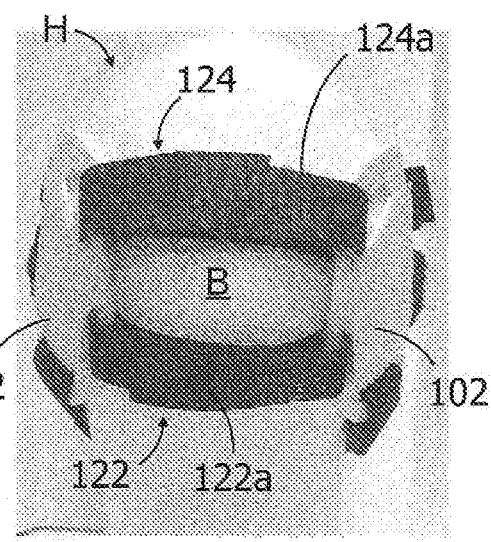
FIG. 10 is a rear view of the apparatus illustrated in FIG. 4 on the head of the user.

The distance between the splints 102 when the forehead strap 116 is pulled tight is controlled by the rear straps 122 and 124. Referring to FIG. 10, the rear straps 122 and 124, which are positioned over the back of the head (or "parietal bone") B, respectively pass through one of the strap apertures 108 on each of the splints. The ends of each rear strap 122 and 124 fold over each other so that hook and loop materials 122b/124b and 122c/124c (or other fasteners) can be secured to one another to fix the length of the rear straps 122 and 124. In at least some instances, the distance between the splints 102 is set prior to the forehead strap 116 being secured in place over the forehead F, although the distance may be adjusted as necessary at any time.

Figure 7:
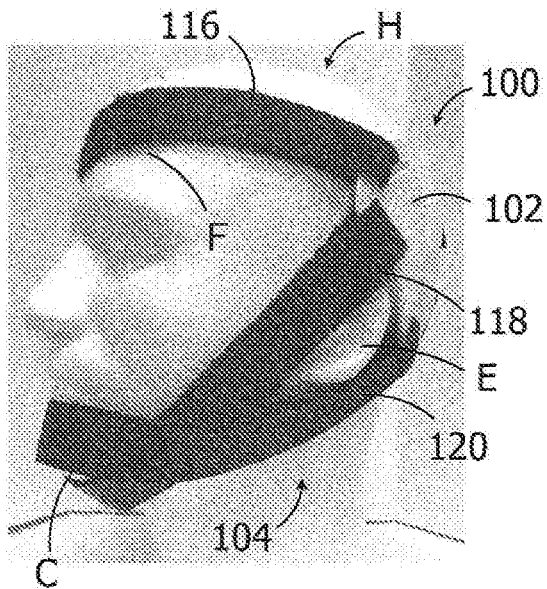
FIG. 7 is a side view of the apparatus illustrated in FIG. 4 on the head of the user.
Figure 8:
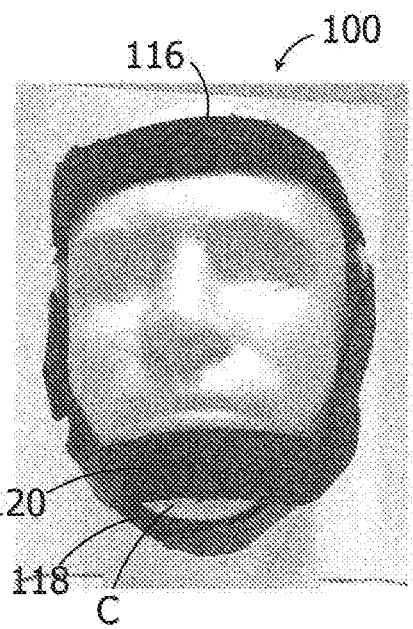
FIG. 8 is a front view of the apparatus illustrated in FIG. 4 on the head of the user.
Figure 9:
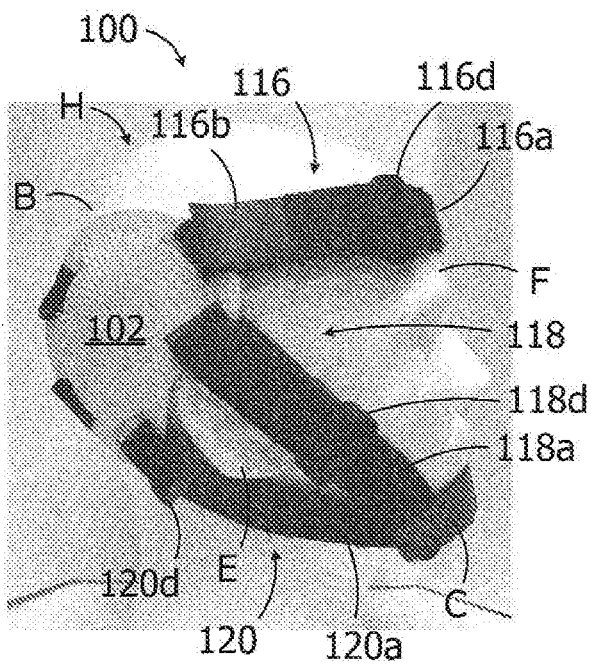
FIG. 9 is a side view of the apparatus illustrated in FIG. 4 on the head of the user.

The chin straps 118 and 120 prevent the splints 102 from moving upwardly beyond their desired locations behind the ears E. Referring to FIGS. 7-9, the associated strap apertures 108 are located such that the chin strap 118 extends from the each splint 102, over or above the ears E and under the chin C, while the chin strap 120 extends from the each splint 102, under the ears E and over the chin C. The chin straps 118 and 120 may also overlap on the chin C in the manner illustrated in FIGS. 12 and 13 below. A portion of the chin strap 118 passes through the buckle 118d and folds over itself so that hook and loop materials 118b and 118c (or other fasteners) can be secured to one another to fix the length/position of the chin strap 118. Similarly, a portion of the chin strap 120 passes through the buckle 120d and folds over itself so that hook and loop materials 120b and 120c (or other fasteners) can be secured to one another to fix the length/position of the chin strap 120. The chin straps 118 and 120 will typically be stretched, and in tension, to pull the splints 102 firmly against the patient's head H and to prevent the splints from sliding upwardly.

Figure 11:
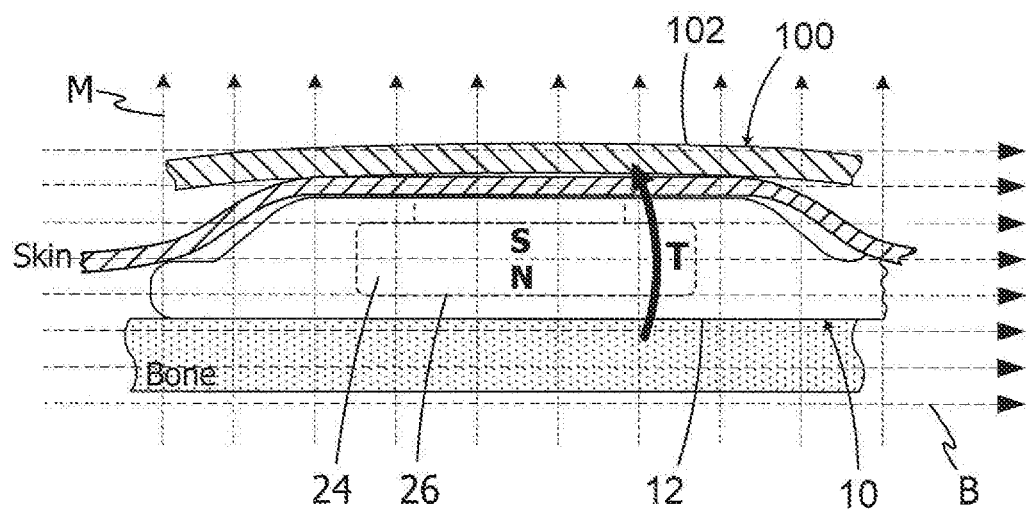
FIG. 11 is a side, partial section view of the apparatus illustrated in FIG. 4 on the head of the user in the presence of a MRI magnetic field.

When worn on the head in the manner illustrated in FIGS. 7-10, with the splints 102 not overlapping the ears and the straps 116-120 tightened, the exemplary apparatus 100 will prevent rotation of a cochlear implant magnet that is exposed to an MRI magnetic field. In particular, and referring to FIG. 11, the strap system 104 has been set in such a manner that the straps pull the splint 102 tightly against the skin over the cochlear implant 10. The splint 102 opposes torque-induced rotational movement of the implant magnet 24, thereby preventing dislodgement and/or reversal of the magnet as well as the pain caused by the associated stress on the dermis.

Figure 12:
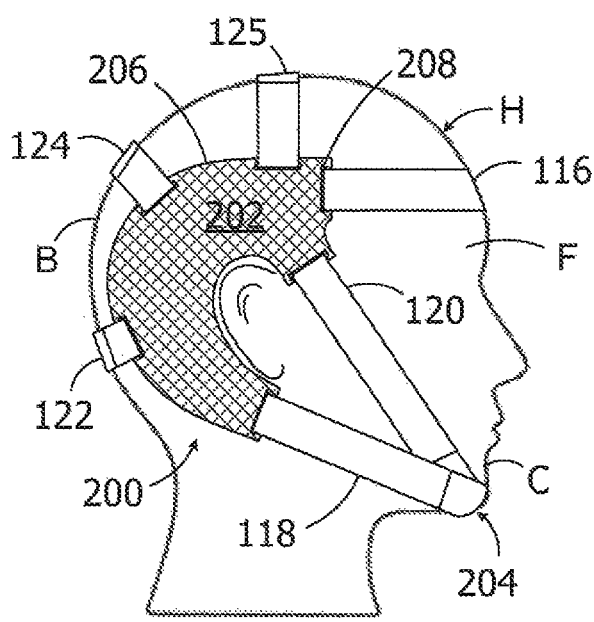
FIG. 12 is a side view of an apparatus in accordance with one embodiment of a present invention on the head of the user.
Figure 13:
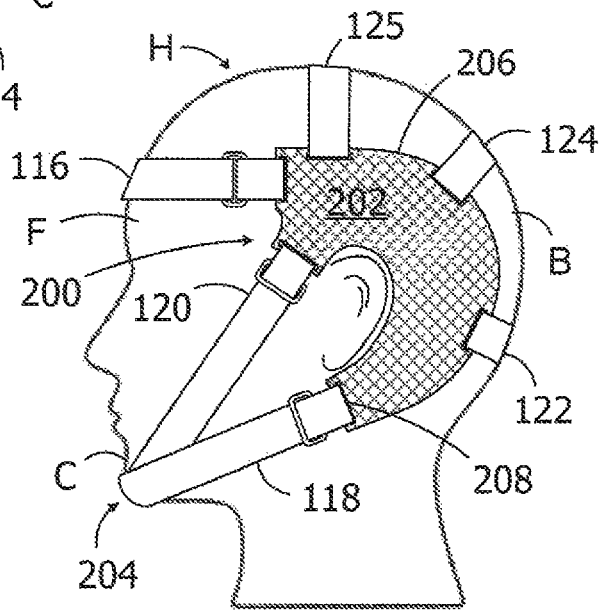
FIG. 13 is a side view of the apparatus illustrated in FIG. 12 on the head of the user.

Another exemplary apparatus is generally represented by reference numeral 200 in FIGS. 12 and 13. The apparatus 200 is substantially similar to apparatus 100 and similar elements are represented by similar reference numerals. For example, the exemplary apparatus 200 includes first and second splints 202 (or only one splint) and a strap system 204 that maintains the splints in their intended locations. The splints 202 include respective splint bodies 206 that may be formed from the same materials as the splint bodies 106 (as shown) or from different materials. The shape of the splints 202 also differs slightly in that, in addition to a curved portion, includes portions that extend above and under the ear, and toward the user's face, to a greater extent than the splints 102. The exemplary strap system 204 is similar to strap system 104 in that strap system 204 includes the aforementioned forehead strap 116 (or "frontal bone strap"), chin straps 118 and 120, and rear straps 122 and 124 (or "parietal bone straps") that extend through apertures 208 in each splint. The strap system 204 also includes a top strap 125 that extends over the top of the head and is otherwise identical to the rear straps 122 and 124. During use, the splints 202 are held tightly over the associated cochlear implant by the strap system 204 to prevent rotation of the implant magnet in the manner described above with reference to FIG. 11.

Figure 14:
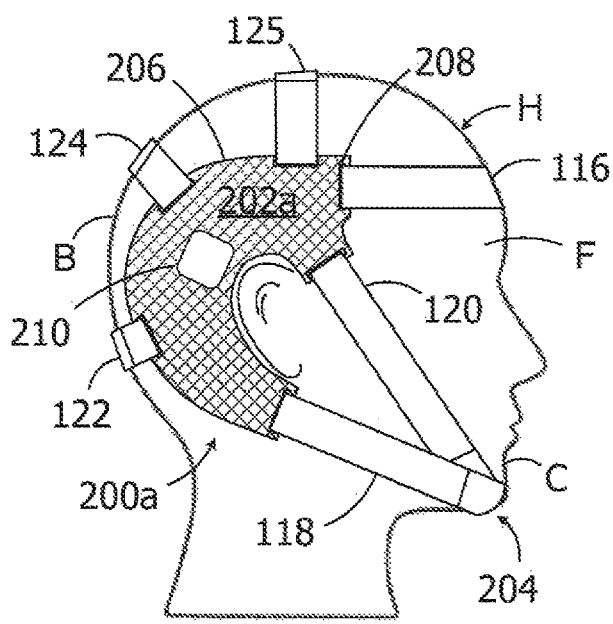
FIG. 14 is a side view of an apparatus in accordance with one embodiment of a present invention on the head of the user.
Figure 15:
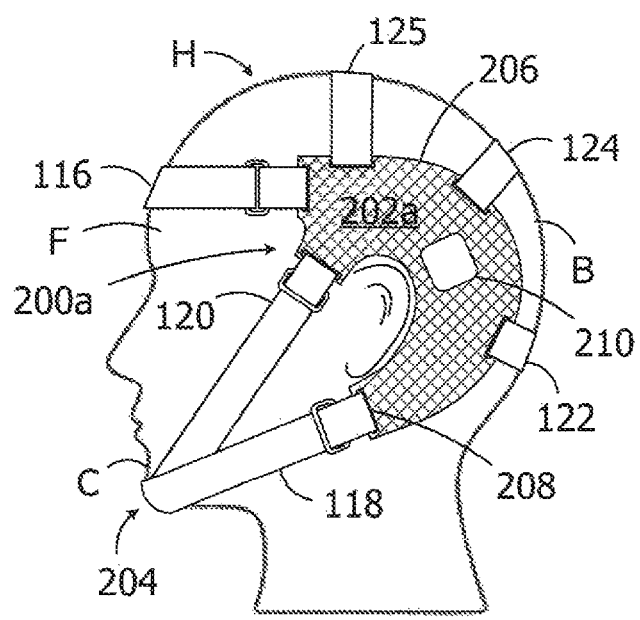
FIG. 15 is a side view of the apparatus illustrated in FIG. 14 on the head of the user.
Figure 16:
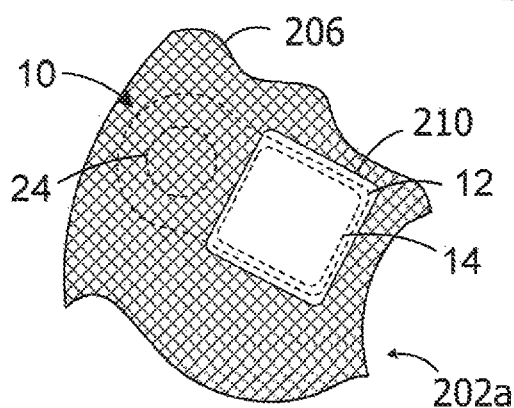
FIG. 16 is an enlarged view showing a portion of the apparatus illustrated in FIGS. 14 and 15 positioned over a cochlear implant.

Still another exemplary apparatus is generally represented by reference numeral 200a in FIGS. 14 and 15. The apparatus 200a is essentially identical to apparatus 200 and similar elements are represented by similar reference numerals. Here, however, each splint 202a includes an aperture 210 that passes through the associated splint body 206. The aperture 210 is located (on the splint body), sized and shaped to reduce the force applied to portions of the associated cochlear implant that do no include the implant magnet. For example, and as illustrated in FIG. 16 in the context of the exemplary cochlear implant 10, the aperture 210 is located, sized and shaped such that it is positioned over the portion of the cochlear implant housing 12 in which the relatively rigid processor assembly 14 is located, and in spaced relation to the magnet, when the straps within straps 122, 124 and 125 are appropriately sized and the straps 116, 118 and 120 tightened.

Figure 17:
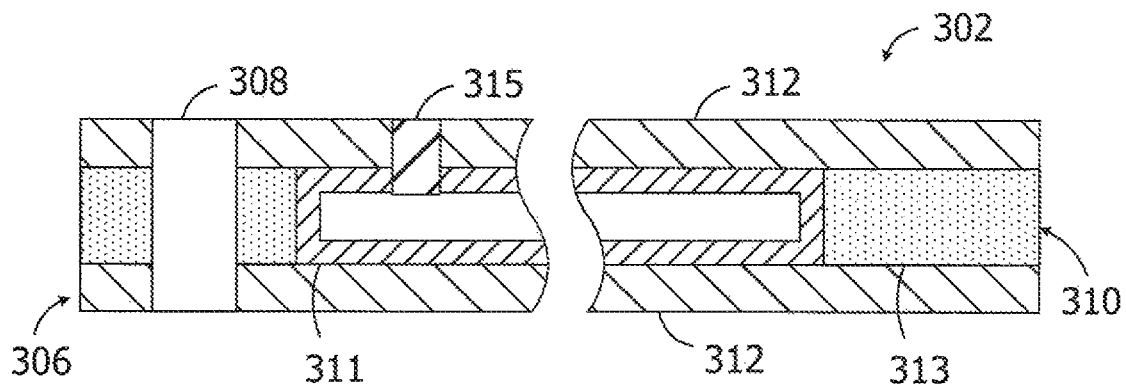
FIG. 17 is a section view of a splint in accordance with one embodiment of a present invention.

In other embodiments, splints may include an inflatable structure to provide localized pressure on the area over the implanted magnet and to improve patient comfort. By way of example, but not limitation, the exemplary splint 302 illustrated in FIG. 17 is substantially similar to splint 102 and similar elements are represented by similar reference numerals. To that end, the splint 302 includes a relatively stiff splint body 306 that is sized and shaped for positioning behind ear. The splint body 306 may be shaped in, for example, a manner similar to the splints 102 or 202, and includes an appropriate number and arrangement of strap apertures 308 to accommodate a strap system such as the strap systems 104 or 204. The splint body 306 may also be a multi-layer structure with an inner layer 310 and outer layers 312 which may have roughened surfaces as described above. Here, however, the inner layer 310 also includes an inflatable bladder 311 formed from rubber or other suitable material, and a border 313 formed from material similar to the material used to form inner layer 110 around the perimeter of the bladder. The bladder 311 may be located inwardly of, or may otherwise offset from, the strap apertures 308. A self-sealing valve 315, such as a septum, may be used to inflate the bladder 311. In other instances (not shown), a bladder may be positioned between a pair of outer layers, formed from nylon or a similar strong and flexible, but not stretchable, material, that are slightly larger than the bladder. The portions of the outer layers that extend beyond the bladder may stitched together to form a border around the bladder and the strap apertures may be formed in the border.

The bladder 311 may be used to provide additional localized pressure to the area over the implanted magnet. For example, an apparatus for opposing torque, which includes a pair of splints 302 and a corresponding strap system, may be positioned on the head in an uninflated state (or an at least substantially uninflated state). The strap system (e.g., strap system 104 or 204) may be used to secure the apparatus in place with the splints 302 behind the ears, and a fluid may be thereafter pumped into the bladder 311 to apply pressure to the area over the implanted magnet.

Figure 18:
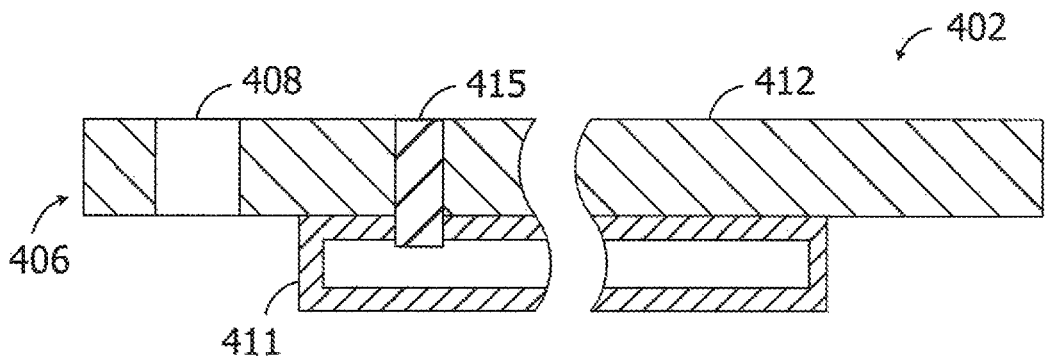
FIG. 18 is a section view of a splint in accordance with one embodiment of a present invention.

Turning to FIG. 18, the exemplary splint 402 is similar to splint 302 and similar elements are represented by similar reference numerals. To that end, the splint 402 includes a relatively stiff splint body 406 that is sized and shaped for positioning behind ear. The splint body 406 may be shaped in, for example, a manner similar to the splints 102 or 202, and includes the appropriate number and arrangement of strap apertures 408 to accommodate a strap system such as the strap systems 104 or 204. Here, however, the splint body 406 includes a single outer layer 412 and an inflatable bladder 411. A self-sealing valve 415, such as a septum, may be used to inflate the bladder 411.

Figure 19:
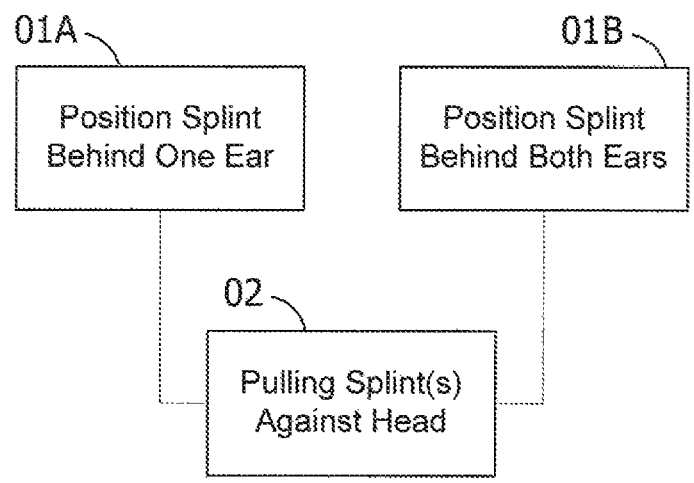
FIG. 19 is a flow chart showing a method in accordance with one embodiment of a present invention.

As discussed above, and referring to FIG. 19, the present methods of preventing magnet rotation may include the steps of positioning a splint behind an ear and over the magnet of an associated cochlear implant (Step 01A), or positioning a first splint behind one ear and over the magnet of an associated cochlear implant as well as positioning a second splint behind to the other ear, either with or without a second cochlear implant behind the second ear (Step 01B). The methods may further include pulling the splint(s) against the head to an extent sufficient to hold the magnet(s) in place without sliding upwardly toward the crown of the head, and maintaining the splint(s) in the desired position(s) (Step 02). For example, the present methods may include positioning the splints 102 behind the ears (or in some instances positioning a single splint behind a single ear) and over at least a first cochlear implant magnet associated with one of the ears (and in some instances over a second cochlear implant magnet associated with the other ear). The forehead strap 116 and chin straps 118 and 120 may then be used to pull the splints 102 against the head. The distance between the splints 102 may be fixed with the rear straps 122 and 124. The splint(s) 102 may be pulled against the head in such a manner that the splint does not overlap the associated ear. After the splint(s) 102 have been pulled against the head and over the magnet(s), and while the patient is being exposed to a MRI magnetic field, cochlear implant magnet rotation will be prevented with the splint(s).

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method of preventing rotation of a first cochlear implant magnet implanted within the head of a patient having first and second ears, the method comprising the steps of:
    positioning an apparatus, including a first splint with a relatively stiff splint body and a strap system with at least a forehead strap and a chin strap that are operably connected to the first splint and are less stiff than the splint body, on the patient's head such that the first splint is located behind the first ear and over the first cochlear implant magnet, the forehead strap is on the forehead and the chin strap is on the chin;
    pulling the first splint against the head with the forehead strap and the chin strap; and
    while the patient is being exposed to an MRI magnetic field, preventing rotation of the first cochlear implant magnet with the first splint.

2. A method as claimed in claim 1, wherein
the apparatus includes a second splint; and
the method further comprises the steps of:
    positioning the second splint behind the second ear, and
    pulling the second splint against the head with the forehead strap and the chin strap.

3. A method as claimed in claim 2, wherein
positioning the second splint comprises positioning the second splint behind the second ear and over a second cochlear implant magnet.

4. A method as claimed in claim 3, further comprising the step of:
    while the patient is being exposed to the MRI magnetic field, preventing rotation of the second cochlear implant magnet with the second splint.

5. A method as claimed in claim 2, wherein
pulling the first splint against the head comprises pulling the first splint against the head with the forehead strap and the chin strap in such a manner that the first splint does not overlap the first ear; and
pulling the second splint against the head comprises pulling the second splint against the head with the forehead strap and the chin strap in such a manner that the second splint does not overlap the second ear.

6. A method as claimed in claim 1, wherein
pulling the first splint against the head comprises pulling the first splint against the head with the forehead strap and the chin strap in such a manner that the first splint does not overlap the first ear.

7. A method of preventing rotation of a first cochlear implant magnet implanted within the head of a patient having first and second ears, the method comprising the steps of:
positioning a first splint behind the first ear and over the first cochlear implant magnet;
positioning a second splint behind the second ear;
pulling the first and second splints against the head with a forehead strap and a chin strap;
fixing the distance between the first splint and the second splint with a rear strap that extends from the first splint to the second splint; and
while the patient is being exposed to an MRI magnetic field, preventing rotation of the first cochlear implant magnet with the first splint.

8. A method as claimed in claim 7, wherein
positioning the second splint comprises positioning the second splint behind the second ear and over a second cochlear implant magnet.

9. A method as claimed in claim 7, further comprising the step of:
while the patient is being exposed to the MRI magnetic field, preventing rotation of the second cochlear implant magnet with the second splint.

10. A method as claimed in claim 7, wherein
pulling the first and second splints against the head comprises pulling the first and second splints against the head with the forehead strap and the chin strap in such a manner that the first splint does not overlap the first ear and the second splint does not overlap the second ear.

11. A method of preventing rotation of a first cochlear implant magnet implanted within the head of a patient having first and second ears, the method comprising the steps of:
positioning an apparatus, including a first splint with a relatively stiff splint body and a plurality of strap apertures and a strap system with at least a forehead strap and a chin strap that extend through the strap apertures and are less stiff than the splint body, on the patient's head such that the first splint is located behind the first ear and over the first cochlear implant magnet;
pulling the first splint against the head with the forehead strap and the chin strap; and
while the patient is being exposed to an MRI magnetic field, preventing rotation of the first cochlear implant magnet with the first splint.

\* \* \* \* \*